United States Patent
Wang et al.

(10) Patent No.: US 11,517,606 B2
(45) Date of Patent: Dec. 6, 2022

(54) COMPOSITION HAVING ANTI-GLYCATION EFFECT AND APPLICATION THEREOF

(71) Applicant: INFINITUS (CHINA) COMPANY LTD., Guangdong (CN)

(72) Inventors: Xiaoling Wang, Guangdong (CN); Huawei Zhu, Guangdong (CN); Zhen Luo, Guangdong (CN); Jian Tang, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 137 days.

(21) Appl. No.: 16/709,929

(22) Filed: Dec. 11, 2019

(65) Prior Publication Data
US 2021/0106642 A1    Apr. 15, 2021

(30) Foreign Application Priority Data
Oct. 15, 2019 (CN) .......................... 201910978544.8

(51) Int. Cl.
| | | |
|---|---|---|
| *A61K 36/63* | (2006.01) | |
| *A61K 8/9789* | (2017.01) | |
| *A61K 8/60* | (2006.01) | |
| *A61K 9/00* | (2006.01) | |
| *A61K 36/61* | (2006.01) | |
| *A61Q 19/08* | (2006.01) | |

(52) U.S. Cl.
CPC .............. *A61K 36/63* (2013.01); *A61K 8/602* (2013.01); *A61K 8/9789* (2017.08); *A61K 9/0053* (2013.01); *A61K 36/61* (2013.01); *A61Q 19/08* (2013.01); *A61K 2800/70* (2013.01)

(58) Field of Classification Search
None
See application file for complete search history.

(56) References Cited

FOREIGN PATENT DOCUMENTS

CN        107080726        8/2017

OTHER PUBLICATIONS

Adams et al. (2006) J. Agric. Food Chem. 54: 980-985, (Year: 2006).*
Bin et al. (2015) Archives of Oral Biology 60: 1030-1038. (Year: 2015).*
Juan et al. (2006) J. Nutr. 136: 2553-2557. (Year: 2006).*
Ye et al. (2017) Journal of Food Science vol. 82, Nr. 8, 1792-1798. (Year: 2017).*

* cited by examiner

*Primary Examiner* — Russell G Fiebig
(74) *Attorney, Agent, or Firm* — JCIP Global Inc.

(57) ABSTRACT

The present invention relates to a composition having an anti-glycation effect and an application thereof. The anti-glycation composition includes the following constituents in parts by mass: 0.1 to 5 parts of *Osmanthus fragrans* extract, 0.1 to 5 parts of *Punica granatum* extract and 0.1 to 2 part of *Olea europaea* extract, wherein in the *Osmanthus fragrans* extract, a mass content of polyphenol is more than or equal to 10%, and a mass content of verbascoside is more than or equal to 10%; in the *Punica granatum* extract, a mass content of polyphenol is more than or equal to 30%, and a mass content of punicalagin is more than or equal to 8%; and in the *Olea europaea* extract, a mass content of polyphenol is more than or equal to 10%, and a mass content of hydroxytyrosol is more than or equal to 3%.

13 Claims, 3 Drawing Sheets

COMPOSITION HAVING ANTI-GLYCATION EFFECT AND APPLICATION THEREOF

CROSS-REFERENCE TO RELATED APPLICATION

This application claims the priority benefit of China application serial no. 201910978544.8, filed on Oct. 15, 2019. The entirety of the above-mentioned patent application is hereby incorporated by reference herein and made a part of this specification.

BACKGROUND

Technical Field

The present invention relates to the field of anti-glycation technologies, and more particularly, to a composition having an anti-glycation effect and an application thereof.

Description of Related Art

Skin is a covering organ composed of dermis, dermal-epidermal junction and epidermis. Like all other organs, the skin undergoes a complicated physiological aging process, which gradually leads to atrophy, dryness, reduction of elasticity and appearance of fine lines and wrinkles of the dermis and the epidermis. As the basis of life, protein indwells in skin, muscle, blood vessels and other parts of a body. In normal adults, 60% of the body is water and 17% to 18% of the body is protein, while tight skin is composed of collagen and elastin in the dermis. Once sugar remained in the body is combined with these proteins, inferior proteins will be formed and advanced glycation end products (AGEs) will be formed, thus resulting in skin glycation. The skin glycation mainly refers to the breakage of collagen fibers of the skin, resulting in relaxation, darkness and yellowing of the skin. In addition, the skin glycation is also prone to cause some inflammatory reactions on the skin, and will also gradually inactivate the collagen. The glycated collagen and elastin will not function normally, thus causing facial laxity and wrinkles. Moreover, the glycation of the dermis will gradually turn the skin yellow, and the glycation of the cuticle is one of the main reasons for skin aging.

The present studies have disclosed some anti-glycation products on the skin. For example, CN107080726A discloses a skin whitening scheme, which relates to anti-glycation food including an *Olea europaea* extract, an *Osmanthus fragrans* extract and an *astragalus* extract.

However, this patent only studies influences of the anti-glycation food on the comprehensive quality of the skin, but does not specifically study the deep mechanism of the skin glycation, and cannot solve the problem of skin glycation well from the internal effects such as the expression of deep glycation products.

SUMMARY

The technical problem to be solved by the present invention is to provide a composition having an anti-glycation effect to overcome the defect and deficiency that the existing anti-glycation products for skin cannot deeply solve skin glycation from the aspect of gene expression.

An object of the present invention is to provide an application of the composition having an anti-glycation effect in preparing anti-glycation products for skin.

Another object of the present invention is to provide a preparation having an anti-glycation effect, wherein the preparation consists of the composition having an anti-glycation effect and other acceptable auxiliary materials.

The above-mentioned objects of the present invention are achieved by the following technical solutions.

A composition having an anti-glycation effect includes the following constituents in parts by mass: 0.1 to 5 parts of *Osmanthus fragrans* extract, 0.1 to 5 parts of *Punica granatum* extract and 0.1 to 2 part of *Olea europaea* extract, wherein, in the *Osmanthus fragrans* extract, a mass content of polyphenol is more than or equal to 10%, and a mass content of verbascoside is more than or equal to 10%;

in the *Punica granatum* extract, a mass content of polyphenol is more than or equal to 30%, and a mass content of punicalagin is more than or equal to 8%; and in the *Olea europaea* extract, a mass content of polyphenol is more than or equal to 10%, and a mass content of hydroxytyrosol is more than or equal to 3%.

In the anti-glycation composition of the present invention, the verbascoside in the *Osmanthus fragrans* extract can inhibit the generation of AGEs (advanced glycation end products), and the inhibition effect is better especially when the content of the verbascoside is more than 10%; moreover, the skin dullness and transparency can be remarkably improved and the skin luster can be increased.

The *Osmanthus fragrans* extract, the *Punica granatum* extract and the *Olea europaea* extract of the present invention all contain polyphenol, and the mass content of polyphenol is more than or equal to 10%; polyphenol substances have the effects of resisting oxidation, scavenging free radicals, resisting inflammation and the like, can effectively accelerate the metabolism speed of sugar, and strengthen and purify the skin.

The punicalagin in the *Punica granatum* extract can also inhibit the generation of AGEs, and also has the effects of preventing a protein structure from being glycated and destroyed, and reducing damages of glycated precursors MGOs to the skin activity and oxidation. When the content of the punicalagin is more than or equal to 10%, the punicalagin can effectively accelerate sugar metabolism, capture free oxygen radicals, effectively resist various oxidative damages, expel turbidity, remove yellowness, as well as brighten, freshen and tender skin.

The hydroxytyrosol in the *Olea europaea* extract can enhance antioxidant capacity; when the content of the hydroxytyrosol is more than or equal to 10%, the hydroxytyrosol can significantly enhance antioxidant effect, inhibit oxidation of primary glycation products to form AGEs, improve skin dullness and unevenness, and brighten the skin.

The prior art has already disclosed that the corresponding *Osmanthus fragrans* extract, the *Punica granatum* extract and the *Olea europaea* extract have certain anti-glycation effects, but the anti-glycation mechanism of the prior art is not clear. The inventor of the present invention inadvertently discovers that the synergistic effect of the *Osmanthus fragrans* extract, the *Punica granatum* extract and the *Olea europaea* extract with specific compatibility and specific quality according to the present invention reduces glycation of fibroblasts, reduces the generation of AGEs and increases the expression of SODs to improve the anti-glycation ability of skin in three dimensions.

The *Osmanthus fragrans* extract, the *Punica granatum* extract and the *Olea europaea* extract of the present invention can be obtained from the market or by extraction.

A method for extracting the *Osmanthus fragrans* extract is as follows:

Dry and pulverized *Osmanthus fragrans* powder is mixed with one or more of water, alcohol and other food processing aids, and subjected to extraction, concentration and drying to obtain the *Osmanthus fragrans* extract. The *Osmanthus fragrans* of the present invention can be selected from *semperflorens* (*Osmanthus fragrans* var. *semperflorens*), *aurantiacus* (*Osmanthus fragrans* (Thunb.) Lour.), *thunbergii* (*Osmanthus fragrans* (Thunb.) Lour) and *odoratus* (*Osmanthus fragrans* cv. *Latifoliu*).

A method for extracting the *Punica granatum* extract is as follows:

Powder obtained by pulverizing *Punica granatum* fruits or drying *Punica granatum* fruit juice is mixed with one or more of water, alcohol and other food processing aids, and subjected to extraction, concentration and drying to obtain the *Punica granatum* extract.

A method for extracting the *Olea europaea* extract is as follows:

Powder obtained by pulverizing *Olea europaeas* or drying *Olea europaea* juice is mixed with one or more of water, alcohol and other food processing aids, and subjected to extraction, concentration and drying to obtain the *Olea europaea* extract.

The mass content of polyphenol, the mass content of verbascoside in the *Osmanthus fragrans*, the mass content of punicalagin in the *Punica granatum* extract and the hydroxytyrosol in the *Olea europaea* extract involved in the present invention are determined by the following methods, specifically:

Determination of polyphenol and verbascoside in the *Osmanthus fragrans* extract refers to a determination method of Q/HSHLY0001S-2018.

The hydroxytyrosol in the *Olea europaea* extract is determined by HPLC, wherein the determination method is as follows:

1. Reagents: methanol (AR), acetonitrile (chromatographically pure), ultrapure water and standard;
2. Standard: hydroxytyrosol (purchased from Tokyo Chemical Industry Co. Ltd., 98%);
3. Instruments and appliances: electronic balance (1/100000), glassware: volumetric flask, 0.45 μm millipore filter and syringe filter, ultrasonic cleaner, high performance liquid chromatograph, Agilent 1100 infusion pump, Agilent 1100 variable-wavelength ultraviolet detector, and Agilent 1100 ChemStation;
4. Chromatographic conditions Chromatographic column: Lnua $C_{ns}$. 250 m×4.6 mm, 5 μm
Mobile phase: acetonitrile (B): water (D)=5:95 (V/V)

| Time (min) | B % | D % |
|---|---|---|
| 0.00 | 5 | 95 |
| 10.00 | 8 | 92 |
| 25.00 | 15 | 85 |
| 26.00 | 5 | 95 |

Flow rate: 1.0 mL/min
Detection wavelength: 276 nm
Sample size: 5μ
Column temperature: 25° C.

5. Operating steps

Preparation of test solution: about 60 mg (20%) of the product is weighed accurately, placed in a 25 ml volumetric flask, and added with 30% methanol, then the mixture is ultrasonically extracted for 15 minutes, cooled to room temperature, then diluted with 30% methanol to a certain volume, shaken evenly, and filtered through a 0.45 μm filter membrane for detection.

Preparation of standard solution: a proper amount of hydroxytyrosol is weighed accurately and added with 30% methanol to prepare a solution with a concentration of about 0.5 mg/ml.

5 μL of the standard solution and 5 μL of the test solution are respectively injected into a HPLC instrument respectively.

6. Result calculation:

$$\text{Content of hydroxytyrosol } (\%) = \frac{A_{sample} \times C_{standard} \times V}{A_{sample} \times M_{standard}} \times P$$

wherein:
$A_{sample}$: peak area of sample;
$A_{standard}$: peak area of standard;
$C_{standard}$: concentration of standard (mg/mL); $M_{standard}$: mass of sample (mg);
$V_{sample}$: certain volume of sample (mL); P: purity of standard (%).

Content of the polyphenol in the *Punica granatum* extract and content of the polyphenol in the *Olea europaea* extract are determined according to Q/WXJ0031 S-2015.

The punicalagin in the *Punica granatum* extract is determined by HPLC, wherein the specific determination method is as follows:

1. Chemical reagents: methanol (chromatographically pure), glacial acetic acid (guaranteed reagent) and distilled water; and standard: punicalagin (98.00%, Sigma-Aldrich).

2. Chromatographic conditions

| | |
|---|---|
| Vacuumizing system | Shimadzu LC-20AT |
| Syringe and autosampler | Shimadzu sil-htc autosampler |
| Probe | Shimadzu SP D-M20A |
| Column | Phenomenex Luna, C18, 5 μm, 4.6 × 150 mm |
| Filtration system | Advance Micro-devices Pvt. Ltd, polytetrafluoroethylene, 0.45 μm |
| Wavelength ($\lambda_{max}$) | 378 nm |
| Injection volume | 20 μL |
| Flow rate | 10 mL/min |
| Mobile phase | Mobile phase A (MPA) |
| | 2% (v/v) aqueous solution of glacial acetic acid |
| | Mobile phase B (MPB) |
| | 2% (v/v) methanol solution of glacial acetic acid |
| Diluent | 2% aqueous solution of glacial acetic acid |
| Separation mode | Gradient separation |

| Gradient design | Time (min) | MP A | MP B |
|---|---|---|---|
| | 0.01 | 99 | 01 |
| | 5.00 | 99 | 01 |
| | 20.00 | 40 | 60 |
| | 26.00 | 22 | 78 |
| | 26.01 | 99 | 01 |
| | 32.00 | 99 | 01 |

3. Preparation of standard solution

Preparation of standard solution of punicalagin: about 5 mg of pure punicalagin is accurately weighed and placed in a 10 ml volumetric flask, added with 5 ml of 2% glacial acetic acid, then the standard is ultrasonically dissolved, diluted to a scale with 2% glacial acetic acid; the solution is thoroughly mixed and filtered with a 0.2 μm membrane filter, and placed in a clean high performance liquid chromatography bottle; 20 μL of the solution is injected and a chromatogram is recorded.

Preparation of sample solution: 150 mg of sample is accurately weighed and placed in a 50 ml volumetric flask, added with 2% glacial acetic acid to a half volume approximately, then the mixture is subjected to ultrasonic treatment for 20 minutes, cooled and diluted to a scale with 2% glacial acetic acid; the solution is thoroughly mixed and filtered with a 0.2 μm membrane filter, and placed in a clean high performance liquid chromatography bottle; 20 μL of the solution is injected and a chromatogram is recorded.

Preparation of mobile phases: mobile phase A (2% (W/V) aqueous solution of glacial acetic acid): a 100 mL volumetric flask is taken, added with 50 mL of water, and 2 mL of glacial acetic acid, and then the mixture is diluted to a certain volume, mixed evenly, and filtered with a 0.45 μm membrane filter.

Mobile phase B (2% (V/V) methanol solution of glacial acetic acid): a 100 mL volumetric flask is taken, added with 50 mL of methanol, and 2 mL of glacial acetic acid; then the mixture is diluted to a certain volume with methanol, mixed evenly, filtered with a 0.45 μm membrane filter, and ultrasonically degassed.

4. Analysis

Given chromatographic conditions are used to record high performance liquid chromatograms of the standard solution and the sample solution prepared above.

The running time of the analysis is 32 minutes, the retention time (RT) of punicalagin-1 is 10.9 minutes, and the retention time of punicalagin-2 is 13.8 minutes. Due to changes in the mobile phase compositions and chromatographic columns, the retention time of analytes may change.

5. Content calculation of punicalagin

Content of punicalagin (%)=sample area×concentration of standard×purity of standard/(area of standard×concentration of standard).

Preferably, the composition includes the following constituents in parts by mass: 0.5 to 3 parts of *Osmanthus fragrans* extract, 0.5 to 5 parts of *Punica granatum* extract and 0.1 to 2 parts of *Olea europaea* extract.

Preferably, the composition includes the following constituents in parts by mass: 1 to 3 parts of *Osmanthus fragrans* extract, 1 to 2 parts of *Punica granatum* extract and 0.1 to 2 parts of *Olea europaea* extract.

For example, the composition may include the following constituents in parts by mass: 3 parts of *Osmanthus fragrans* extract, 1 part of *Punica granatum* extract and 0.1 part of *Olea europaea* extract;

2 parts of *Osmanthus fragrans* extract, 5 parts of *Punica granatum* extract and 1 part of *Olea europaea* extract;

0.5 part of *Osmanthus fragrans* extract, 0.5 part of *Punica granatum* extract and 1 part of *Olea europaea* extract;

or, 2 parts of *Osmanthus fragrans* extract, 2 parts of *Punica granatum* extract and 0.1 part of *Olea europaea* extract.

Further, the composition includes the following constituents in parts by mass: 3 parts of *Osmanthus fragrans* extract, 1 part of *Punica granatum* extract and 0.1 part of *Olea europaea* extract.

Preferably, in the composition:

in the *Osmanthus fragrans* extract, the mass content of polyphenol is 10%, and the mass content of verbascoside is 10%;

in the *Punica granatum* extract, the mass content of polyphenol is 30%, and the mass content of punicalagin is 10%; and in the *Olea europaea* extract, the mass content of polyphenol is 10%, and the mass content of hydroxytyrosol is 3%.

Use of the above-mentioned composition having an anti-glycation effect in preparing anti-glycation products for skin also falls within the scope of protection of the present invention.

The present invention further protects a preparation having an anti-glycation effect, wherein the preparation consists of the composition having an anti-glycation effect and other acceptable auxiliary materials.

It should be noted that the other acceptable auxiliary materials of the present invention are auxiliary materials commonly used in commercially available products at current for preparing a specific preparation.

The preparation having an anti-glycation effect of the present invention may be a beverage preparation, a skin care product, and food or health care product;

the food or health care product includes: liquid food or health care product, or solid or semi-solid food or health care product;

wherein the liquid food or health care product includes: beverage, oral liquid or milk; and the solid or semi-solid liquid food or health care product includes: biscuits, cakes, granules, candy, chocolate, jelly, jam, canned food and gel.

Compared with the prior art, the present invention has the beneficial effects as follows:

The present invention provides a composition having an anti-glycation effect which includes the *Osmanthus fragrans* extract, the *Punica granatum* extract and the *Olea europaea* extract, and the polyphenol substances in the composition have the effects of resisting oxidation, scavenging free radicals, resisting inflammation and the like. The verbascoside and the punicalagin can inhibit the generation of AGEs, prevent protein structures from being destroyed by glycation, reduce the damage of glycated precursors MGOs to skin activity and oxidation, and the hydroxytyrosol of the *Olea europaea* extract can improve the antioxidant capacity and significantly enhance the antioxidant effect.

The synergistic effect of the *Osmanthus fragrans* extract, the *Punica granatum* extract and the *Olea europaea* extract with specific compatibility and specific quality according to the invention significantly reduces the generation of CMLs which are glycation end products of fibroblasts, reduces the generation of AGEs and increases the expression of SODs to improve the anti-glycation ability of skin in three dimensions.

DESCRIPTION OF THE EMBODIMENTS

The invention is further described hereinafter with reference to the specific embodiments, but the embodiments are not intended to limit the invention in any form. Unless defined otherwise, the raw material reagents used in the embodiments of the invention are conventionally purchased raw material reagents.

Embodiment 1

A composition having an anti-glycation effect includes the following constituents in parts by mass: 3 parts of *Osmanthus fragrans* extract, 1 part of *Punica granatum* extract and 0.1 part of *Olea europaea* extract.

In the *Osmanthus fragrans* extract, a mass content of polyphenol is 10%, and a mass content of verbascoside is 10%;

in the *Punica granatum* extract, a mass content of polyphenol is 30%, and a mass content of punicalagin is 10%; and in the *Olea europaea* extract, a mass content of polyphenol is 10%, and a mass content of hydroxytyrosol is 3%.

A method for extracting the *Osmanthus fragrans* extract was as follows:

Dry and pulverized *Osmanthus fragrans* powder was mixed with one or more of water, alcohol and other food processing aids, and subjected to extraction, concentration and drying to obtain the *Osmanthus fragrans* extract. The *Osmanthus fragrans* of the present invention may be selected from *semperflorens* (*Osmanthus fragrans* var. *semperflorens*), *aurantiacus* (*Osmanthus fragrans* (Thunb.) Lour.), *thunbergii* (*Osmanthus fragrans* (Thunb.) Lour) and *odoratus* (*Osmanthus fragrans* cv. *Latifoliu*).

A method for extracting the *Punica granatum* extract was as follows:

Powder obtained by pulverizing *Punica granatum* fruits or drying *Punica granatum* fruit juice was mixed with one or more of water, alcohol and other food processing aids, and subjected to extraction, concentration and drying to obtain the *Punica granatum* extract.

A method for extracting the *Olea europaea* extract was as follows:

Powder obtained by pulverizing *Olea europaeas* or drying *Olea europaea* juice was mixed with one or more of water, alcohol and other food processing aids, and subjected to extraction, concentration and drying to obtain the *Olea europaea* extract.

Determination of polyphenol and verbascoside in the *Osmanthus fragrans* extract referred to a determination method of Q/HSHLY0001S-2018.

The hydroxytyrosol in the *Olea europaea* extract was determined by a HPLC method, wherein the determination method was as follows:

1. Reagents: methanol (AR), acetonitrile (chromatographically pure), ultrapure water and standard;
2. Standard: hydroxytyrosol (purchased from Tokyo Chemical Industry Co. Ltd., 98%);
3. Instruments and appliances: electronic balance (1/100000), glassware: volumetric flask, 0.45 μm millipore filter and syringe filter, ultrasonic cleaner, high performance liquid chromatograph, Agilent 1100 infusion pump, Agilent 1100 variable-wavelength ultraviolet detector, and Agilent 1100 ChemStation;
4. Chromatographic conditions Chromatographic column: Lnua Cns. 250 m×4.6 mm, 5 μm
Mobile phase: acetonitrile (B): water (D)=5:95 (V/V)

| Time (min) | B % | D % |
|---|---|---|
| 0.00 | 5 | 95 |
| 10.00 | 8 | 92 |
| 25.00 | 15 | 85 |
| 26.00 | 5 | 95 |

Flow rate: 1.0 mL/min
Detection wavelength: 276 nm
Sample size: 5μ
Column temperature: 25° C.

5. Operating steps

Preparation of test solution: about 60 mg (20%) of the product was weighed accurately, placed in a 25 ml volumetric flask, and added with 30% methanol, then the mixture was ultrasonically extracted for 15 minutes, cooled to room temperature, then diluted to a certain volume with 30% methanol, shaken evenly, and filtered through a 0.45 μm filter membrane for detection.

Preparation of standard solution: a proper amount of hydroxytyrosol was weighed accurately and added with 30% methanol to prepare a solution with a concentration of about 0.5 mg/mL.

5 μL of the standard solution and 5 μL of the test solution were respectively injected into a HPLC instrument respectively.

6. Result calculation:

$$\text{Content of hydroxytyrosol }(\%) = \frac{A_{sample} \times C_{standard} \times V}{A_{sample} \times M_{standard}} \times P$$

wherein:
$A_{sample}$: peak area of sample;
$A_{standard}$: peak area of standard;
$C_{standard}$: concentration of standard (mg/mL); Mn: mass of sample (mg);
$V_{sample}$: certain volume of sample (mL); P: purity of standard (%).

Content of the polyphenol in the *Punica granatum* extract and content of the polyphenol in the *Olea europaea* extract were determined according to Q/WXJ0031 S-2015.

The punicalagin in the *Punica granatum* extract was determined by HPLC, wherein the specific determination method was as follows:

1. Chemical reagents: methanol (chromatographically pure), glacial acetic acid (guaranteed reagent) and distilled water; and standard: punicalagin (98.00%, Sigma-Aldrich)
2. Chromatographic conditions

| | |
|---|---|
| Vacuumizing system | Shimadzu LC-20AT |
| Syringe and autosampler | Shimadzu sil-htc autosampler |
| Probe | Shimadzu SP D-M20A |
| Column | Phenomenex Luna, C18, 5 μm, 4.6 × 150 mm |
| Filtration system | Advance Micro-devices Pvt. Ltd, polytetrafluoroethylene, 0.45 μm |
| Wavelength ($\lambda_{max}$) | 378 nm |
| Injection volume | 20 μL |
| Flow rate | 10 mL/min |
| Mobile phase | Mobile phase A (MPA) 2% (v/v) aqueous solution of glacial acetic acid Mobile phase B (MPB) 2% (v/v) methanol solution of glacial acetic acid |
| Diluent | 2% aqueous solution of glacial acetic acid |
| Separation mode | Gradient separation |

| Gradient design | Time (min) | MP A | MP B |
|---|---|---|---|
| | 0.01 | 99 | 01 |
| | 5.00 | 99 | 01 |
| | 20.00 | 40 | 60 |
| | 26.00 | 22 | 78 |
| | 26.01 | 99 | 01 |
| | 32.00 | 99 | 01 |

3. Preparation of standard solution:

Preparation of standard solution of punicalagin: about 5 mg of pure punicalagin was accurately weighed and placed in a 10 ml volumetric flask, added with 5 ml of 2% glacial acetic acid, then the standard was ultrasonically dissolved, diluted to a scale with 2% glacial acetic acid; the solution was thoroughly mixed and filtered with a 0.2 μm membrane filter, and placed in a clean high performance liquid chromatography bottle; 20 μL of the solution was injected and a chromatogram was recorded.

Preparation of sample solution: 150 mg of pure sample was accurately weighed and placed in a 50 ml volumetric flask, added with 2% glacial acetic acid to a half volume approximately, then the mixture was subjected to ultrasonic treatment for 20 minutes, cooled and diluted to a scale with 2% glacial acetic acid; the solution was thoroughly mixed and filtered with a 0.2 μm membrane filter, and placed in a clean high performance liquid chromatography bottle; 20 μL of the solution was injected and a chromatogram was recorded.

Preparation of mobile phases: mobile phase A (2% (V/V) aqueous solution of glacial acetic acid): a 100 mL volumetric flask was taken, added with 50 mL of water, and 2 mL of glacial acetic acid, and then the mixture was diluted to a certain volume, mixed evenly, and filtered with a 0.45 μm membrane filter.

Mobile phase B (2% (V/V) methanol solution of glacial acetic acid): a 100 mL volumetric flask was taken, added with 50 mL of methanol, and 2 mL of glacial acetic acid; then the mixture was diluted to a certain volume with methanol, mixed evenly, filtered with a 0.45 μm membrane filter, and ultrasonically degassed.

4. Analysis

Given chromatographic conditions were used to record high performance liquid chromatograms of the standard solution and the sample solution prepared above.

The running time of the analysis was 32 minutes, the retention time (RT) of punicalagin-1 was 10.9 minutes, and the retention time of punicalagin-2 was 13.8 minutes. Due to changes in the mobile phase compositions and chromatographic columns, the retention time of analytes may change.

5. Content calculation of punicalagin

Content of punicalagin (%)=sample area×concentration of standard×purity of standard/(area of standard×concentration of standard).

Embodiment 2

A composition having an anti-glycation effect includes the following constituents in parts by mass: 2 parts of *Osmanthus fragrans* extract, 5 parts of *Punica granatum* extract and 1 part of *Olea europaea* extract;

wherein, the *Osmanthus fragrans* extract, the *Punica granatum* extract and the *Olea europaea* extract are the same as that in the embodiment 1.

Embodiment 3

A composition having an anti-glycation effect includes the following constituents in parts by mass: 1 part of *Osmanthus fragrans* extract, 2 parts of *Punica granatum* extract and 2 parts of *Olea europaea* extract, wherein, the *Osmanthus fragrans* extract, the *Punica granatum* extract and the *Olea europaea* extract are the same as that in the embodiment 1.

Embodiment 4

A composition having an anti-glycation effect includes the following constituents in parts by mass: 0.5 part of *Osmanthus fragrans* extract, 0.5 part of *Punica granatum* extract and 1 part of *Olea europaea* extract, wherein, the *Osmanthus fragrans* extract, the *Punica granatum* extract and the *Olea europaea* extract are the same as that in the embodiment 1.

Embodiment 5

A composition having an anti-glycation effect includes the following constituents in parts by mass: 2 parts of *Osmanthus fragrans* extract, 2 parts of *Punica granatum* extract and 0.1 part of *Olea europaea* extract, wherein, the *Osmanthus fragrans* extract, the *Punica granatum* extract and the *Olea europaea* extract are the same as that in the embodiment 1.

Embodiment 6

A composition having an anti-glycation effect includes the following constituents in parts by mass: 3 parts of *Osmanthus fragrans* extract, 1 part of *Punica granatum* extract and 0.1 part of *Olea europaea* extract.

wherein, in the *Osmanthus fragrans* extract, a mass content of polyphenol is 10%, and a mass content of verbascoside is 10%;

in the *Punica granatum* extract, a mass content of polyphenol is 40%, and a mass content of punicalagin is 8%; and in the *Olea europaea* extract, a mass content of polyphenol is 10%, and a mass content of hydroxytyrosol is 3%.

Comparative Example 1

An extract having an anti-glycation effect, wherein the extract is an *Osmanthus fragrans* extract.

Comparative Example 2

An extract having an anti-glycation effect, wherein the extract is a *Punica granatum* extract.

Comparative Example 3

An extract having an anti-glycation effect, wherein the extract is an *Olea europaea* extract.

Comparative Example 4

A composition having an anti-glycation effect includes the following constituents in parts by mass: 3 parts of *Osmanthus fragrans* extract, 1 part of *Punica granatum* extract and 0.1 part of *Olea europaea* extract.

wherein, in the *Osmanthus fragrans* extract, a mass content of polyphenol is 8%, and a mass content of verbascoside is 8%;

in the *Punica granatum* extract, a mass content of polyphenol is 40%, and a mass content of punicalagin is 10%; and in the *Olea europaea* extract, a mass content of polyphenol is 10%, and a mass content of hydroxytyrosol is 3%.

Comparative Example 5

A composition having an anti-glycation effect includes the following constituents in parts by mass: 3 parts of *Osmanthus fragrans* extract, 1 part of *Punica granatum* extract and 0.1 part of *Olea europaea* extract, wherein, in the *Osmanthus fragrans* extract, a mass content of polyphenol is 8%, and a mass content of verbascoside is 8%;

in the *Punica granatum* extract, a mass content of polyphenol is 20%, and a mass content of punicalagin is 8%; and in the *Olea europaea* extract, a mass content of polyphenol is 8%, and a mass content of hydroxytyrosol is 2%.

Result Detection (1) Verification and Test of Anti-Glycation Ability of Sample by Using Skin Cells Analysis on Expression of Glycation Marker Gene in Skin Fibroblasts:

N-ε-carboxy methyl lysine (CML) was an advanced glycation end product, and the glycation degree of the skin cells was reflected by detecting a CML level.

Detection Method:

Fibroblasts were seeded in a 24-well plate and treated with 400 μM methylglyoxal and glyoxal to induce glycation. After the cells were treated with a sample group for 7 days, an immunofluorescence experiment was carried out. 800 μM aminoguanidine was a positive control, and experimental groups were compositions of the embodiments and the comparative examples with a mass concentration of 0.01%.

The expression of CMLs after treatment with active ingredients was observed.

Figure 1:
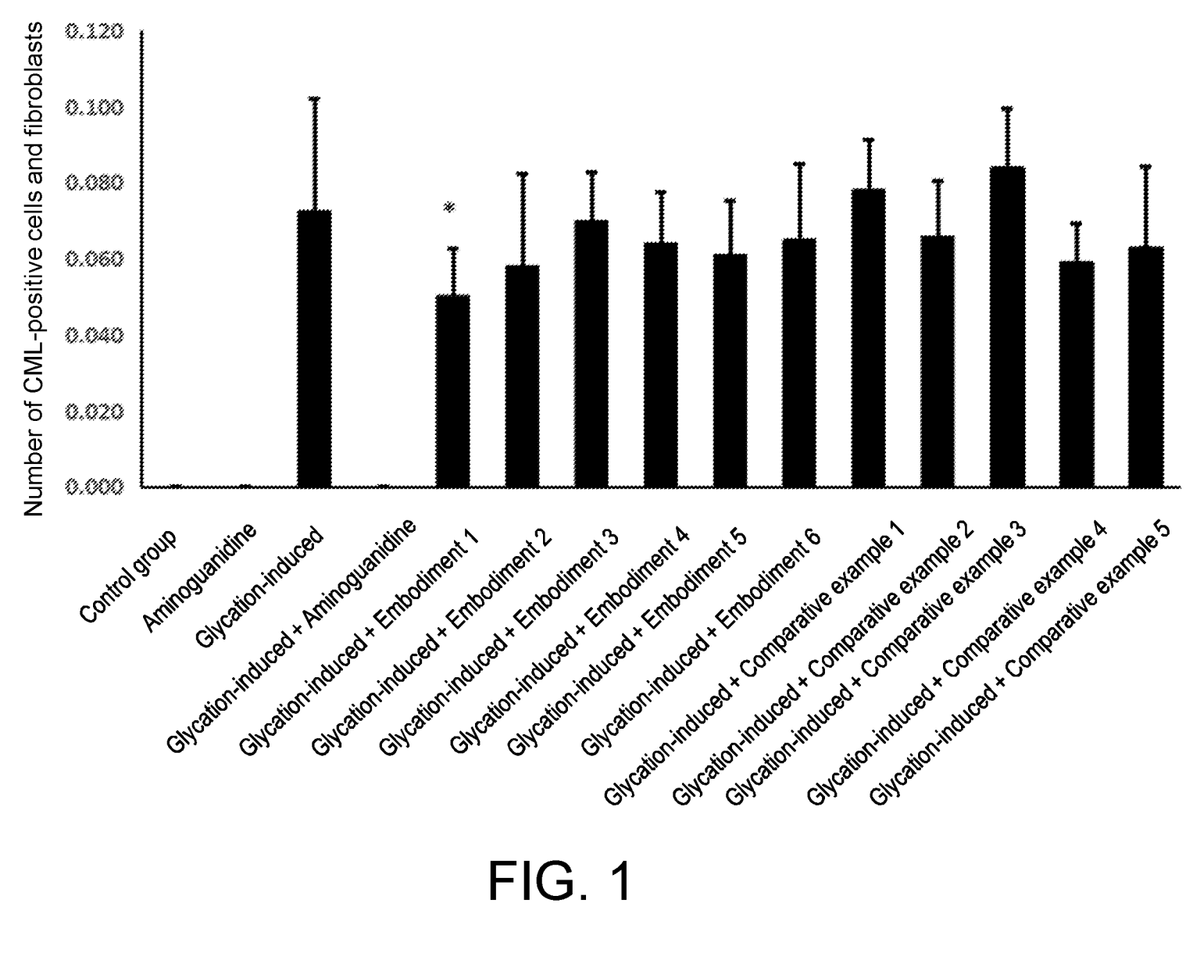
FIG. 1 shows expression of CMLs in glycation-induced fibroblasts.

Results are shown in FIG. 1, wherein histograms show the analysis results on red pixels after fluorescence microscope shooting. The Embodiment 1 has the most significant effect on reducing a glycation reaction of the fibroblasts.

(2) Verification and Test of the Anti-Glycation Ability of Test Sample by Using a Mouse Aging Model D-galactose (1 g/kg) was used to make the model. D-galactose was freshly prepared and used every day. A normal group received subcutaneous injection of physiological saline with the same administration volume of 0.1 mL/10 g, and continuously received daily subcutaneous injection on the back for 42 days. The test samples (compositions of the embodiments and the comparison examples) were administered by gavage every day; and an induction group was given normal saline every day. After 42 days, the animals were killed to take blood for detecting biochemical indexes and pathology (SOD activity, AGEs).

Figure 2:
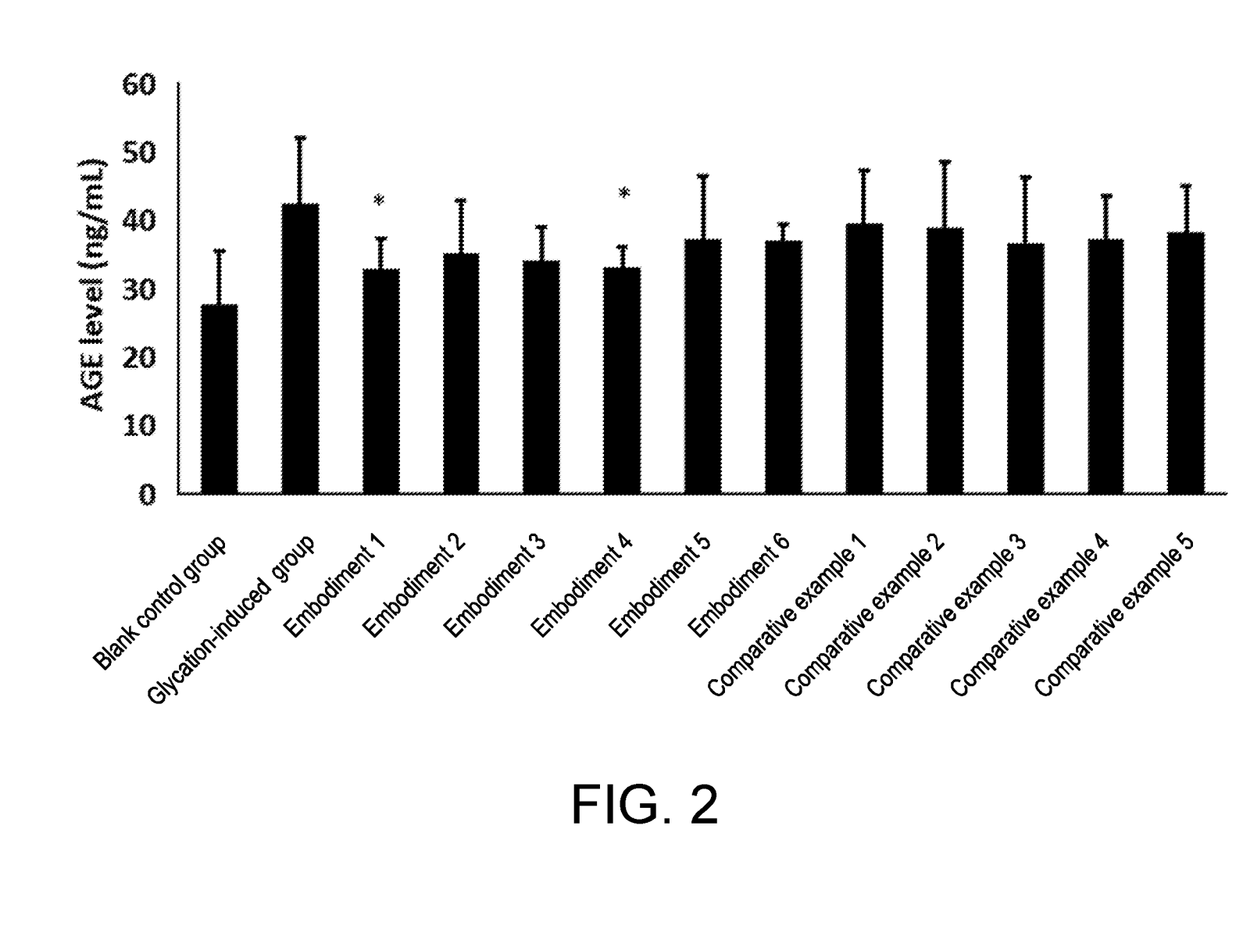
FIG. 2 shows expression of AGEs in an aging mouse model.
Figure 3:
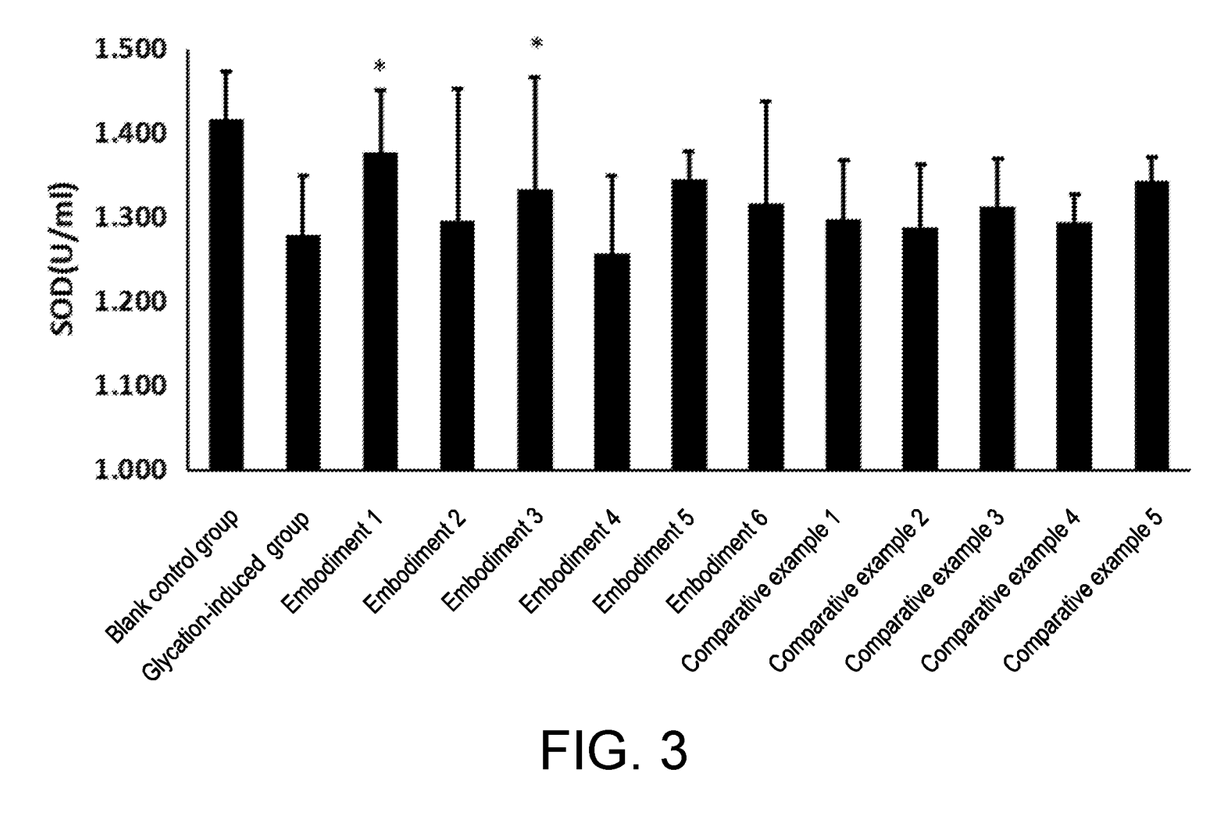
FIG. 3 shows expression of SOD in the aging mouse model.

Results are shown in FIG. 2 and FIG. 3, wherein the Embodiment 1 has the most significant effect on reducing the generation of AGEs and increasing the expression of SODs in the aging mice.

(3) Data Processing

All the groups were compared with a glycation-induced control group for significant difference analysis, and T test was used for statistical difference analysis. The results are shown in Table 1 and Table 2. Results are indicated by asterisks *P<0.05; P<0.01; and *P<0.001.

TABLE 1

|  | CML % | AGE/ng/mL | SOD/U/mL |
|---|---|---|---|
| Blank control | 0 ± 0<br>P = 0.002 | 27.83 ± 7.76<br>P = 0.001 | 1.415 ± 0.058<br>P = 0.004 |
| Glycation-induced control group | 0.072 ± 0.03 | 42.42 ± 9.53 | 1.279 ± 0.070 |
| Embodiment 1 | 0.050 ± 0.012<br>P = 0.014 | 33.00 ± 9.46<br>P = 0.022 | 1.377 ± 0.033<br>P = 0.033 |
| Embodiment 2 | 0.058 ± 0.025<br>P = 0.061 | 34.28 ± 5.63<br>P = 0.053 | 1.295 ± 0.818<br>P = 0.818 |
| Embodiment 3 | 0.070 ± 0.013<br>P = 0.245 | 34.10 ± 4.96<br>P = 0.052 | 1.333 ± 0.401<br>P = 0.401 |
| Embodiment 4 | 0.064 ± 0.013<br>P = 0.168 | 33.20 ± 2.95<br>P = 0.049 | 1.256 ± 0.647<br>P = 0.647 |

TABLE 1-continued

|  | CML % | AGE/ng/mL | SOD/U/mL |
|---|---|---|---|
| Embodiment 5 | 0.061 ± 0.014<br>P = 0.165 | 37.35 ± 9.08<br>P = 0.238 | 1.346 ± 0.043<br>P = 0.043 |
| Embodiment 6 | 0.069 ± 0.02<br>P = 0.162 | 36.98 ± 2.46<br>0.32 | 1.32 ± 0.12<br>0.103 |
| Comparative example 1 | 0.078 ± 0.013<br>P = 0.326 | 39.57 ± 7.76<br>P = 0.312 | 1.298 ± 0.070<br>P = 0.762 |
| Comparative example 2 | 0.066 ± 0.014<br>P = 0.232 | 38.92 ± 9.53<br>P = 0.247 | 1.288 ± 0.075<br>P = 0.659 |
| Comparative example 3 | 0.084 ± 0.015<br>P = 0.363 | 36.74 ± 9.46<br>P = 0.179 | 1.312 ± 0.16<br>P = 0.085 |
| Comparative example 4 | 0.063 ± 0.01<br>P = 0.126 | 37.19 ± 6.29<br>0.301 | 1.29 ± 0.03<br>0.1821 |
| Comparative example 5 | 0.059 ± 0.02<br>P = 0.102 | 38.23 ± 6.75<br>P = 0.242 | 1.34 ± 0.03<br>P = 0.1213 |

From the data in Table 1 above, it can be seen that the anti-glycation composition provided by the present invention can well inhibit the generation of AGEs which are glycation end products, through the synergistic effect of the *Osmanthus fragrans* extract, the *Punica granatum* extract and the *Olea europaea* extract. The content of the AGEs is close to 27.83±7.76 in a blank group, which is significantly lower than 42.42±9.53 in the glycation-induced control group. The corresponding advanced glycation end products CMLs of the fibroblasts are also significantly reduced, and the expression effect of SODs is significantly increased. The anti-glycation ability of skin is improved from three dimensions of CMLs, AGEs and SODs.

Obviously, the above-mentioned embodiments of the invention are merely examples for clearly illustrating the invention, but are not intended to limit the implementations of the invention. For those of ordinary skills in the art, other different forms of changes or variations can be made on the basis of the above description. It is not necessary or possible to exhaust all the embodiments here. Any change, equivalent substitution, and improvement made within the spirit and principle of the invention shall fall within the protection scope of the claims of the invention.

What is claimed is:

1. A skin care emulsion, comprising the constituents in parts by mass in the following ratio:
   0.5 to 3 parts of *Osmanthus fragrans* extract;
   0.5 to 5 parts of *Punica granatum* extract; and
   0.1 to 2 parts of *Olea europaea* extract,
   wherein in the *Osmanthus fragrans* extract, a mass content of polyphenol is more than or equal to 10%, and a mass content of verbascoside is more than or equal to 10%;
   in the *Punica granatum* extract, a mass content of polyphenol is more than or equal to 30%, and a mass content of punicalagin is more than or equal to 10%; and
   in the *Olea europaea* extract, a mass content of polyphenol is more than or equal to 10%, and a mass content of hydroxytyrosol is more than or equal to 3%,
   wherein the skin care emulsion has an anti-glycation effect.

2. The skin care emulsion according to claim 1, wherein the skin care emulsion comprises the following constituents in parts by mass: 1 to 3 parts of *Osmanthus fragrans* extract, 1 to 2 parts of *Punica granatum* extract and 0.1 to 2 parts of *Olea europaea* extract.

3. The skin care emulsion according to claim 2, wherein the skin care emulsion comprises the following constituents in parts by mass: 3 parts of *Osmanthus fragrans* extract, 1 part of *Punica granatum* extract and 0.1 part of *Olea europaea* extract.

4. The skin care emulsion according to claim 3, wherein in the skin care emulsion:
- in the *Osmanthus fragrans* extract, the mass content of polyphenol is 10%, and the mass content of verbascoside is 10%;
- in the *Punica granatum* extract, the mass content of polyphenol is 30%, and the mass content of punicalagin is 10%; and
- in the *Olea europaea* extract, the mass content of polyphenol is 10%, and the mass content of hydroxytyrosol is 3%.

5. A method of preparing anti-glycation products for skin, comprising using the skin care emulsion according to claim 1.

6. A preparation, wherein the preparation consists of the skin care emulsion according to claim 1 and other acceptable auxiliary materials.

7. A method of preparing anti-glycation products for skin, comprising using the skin care emulsion according to claim 2.

8. A method of preparing anti-glycation products for skin, comprising using the skin care emulsion according to claim 3.

9. A method of preparing anti-glycation products for skin, comprising using the skin care emulsion according to claim 4.

10. A preparation, wherein the preparation consists of the skin care emulsion according to claim 2 and other acceptable auxiliary materials.

11. A preparation, wherein the preparation consists of the skin care emulsion according to claim 3 and other acceptable auxiliary materials.

12. A skin care cream, comprising the constituents in parts by mass in the following ratio:
- 0.5 to 3 parts of *Osmanthus fragrans* extract;
- 0.5 to 5 parts of *Punica granatum* extract; and
- 0.1 to 2 parts of *Olea europaea* extract,
- wherein in the *Osmanthus fragrans* extract, a mass content of polyphenol is more than or equal to 10%, and a mass content of verbascoside is more than or equal to 10%;
- in the *Punica granatum* extract, a mass content of polyphenol is more than or equal to 30%, and a mass content of punicalagin is more than or equal to 10%; and
- in the *Olea europaea* extract, a mass content of polyphenol is more than or equal to 10%, and a mass content of hydroxytyrosol is more than or equal to 3%,
- wherein the skin care cream has an anti-glycation effect.

13. A skin care lotion, comprising the constituents in parts by mass in the following ratio:
- 0.5 to 3 parts of *Osmanthus fragrans* extract;
- 0.5 to 5 parts of *Punica granatum* extract; and
- 0.1 to 2 parts of *Olea europaea* extract,
- wherein in the *Osmanthus fragrans* extract, a mass content of polyphenol is more than or equal to 10%, and a mass content of verbascoside is more than or equal to 10%;
- in the *Punica granatum* extract, a mass content of polyphenol is more than or equal to 30%, and a mass content of punicalagin is more than or equal to 10%; and
- in the *Olea europaea* extract, a mass content of polyphenol is more than or equal to 10%, and a mass content of hydroxytyrosol is more than or equal to 3%,
- wherein the skin care lotion has an anti-glycation effect.

* * * * *